United States Patent [19]
Slater et al.

[11] Patent Number: 6,146,511
[45] Date of Patent: Nov. 14, 2000

[54] ELECTROPHORETIC NUCLEIC ACID PURIFICATION METHOD

[75] Inventors: Gary Slater, Ottawa, Canada; J. William Efcavitch, San Mateo, Calif.; Guy Drouin, Gatineau, Canada; Pascal Mayer, Eloise, France; Jean Rousseau, Quebec; Hong Yan Zhou, Ottawa, both of Canada; Claudia Chiesa, Foster City, Calif.; Robert Ruhfel, San Francisco, Calif.; Roger O'Neill, San Carlos, Calif.

[73] Assignees: The Perkin-Elmer Corporation, Foster City, Calif.; The University of Ottawa, Ottawa, Canada

[21] Appl. No.: 09/016,531

[22] Filed: Jan. 30, 1998

[51] Int. Cl.$^7$ ..................................................... G01N 27/26
[52] U.S. Cl. ........................................... 204/457; 204/466
[58] Field of Search ................................... 204/456, 457, 204/458, 466

[56] References Cited

U.S. PATENT DOCUMENTS

| | | | |
|---|---|---|---|
| 4,624,769 | 11/1986 | Simada et al. | 204/606 |
| 5,139,637 | 8/1992 | MacConnell . | |
| 5,209,831 | 5/1993 | MacConnell . | |
| 5,217,593 | 6/1993 | MacConnell . | |
| 5,284,940 | 2/1994 | Lin et al. . | |
| 5,286,434 | 2/1994 | Slater et al. | 204/457 |
| 5,384,022 | 1/1995 | Rajasekram | 204/616 |
| 5,482,836 | 1/1996 | Cantor et al. . | |
| 5,501,963 | 3/1996 | Burckhardt . | |
| 5,538,614 | 7/1996 | Han . | |
| 5,587,062 | 12/1996 | Togawa et al. . | |
| 5,650,055 | 7/1997 | Margolis . | |

FOREIGN PATENT DOCUMENTS

| | | | |
|---|---|---|---|
| 0 545 689 A1 | 6/1993 | European Pat. Off. | G01N 27/447 |
| 0 644 420 A2 | 3/1995 | European Pat. Off. | G01N 27/447 |
| 0 773 225 A2 | 5/1997 | European Pat. Off. | C07H 1/08 |
| WO 86/00989 | 2/1986 | WIPO | G01N 27/26 |
| WO 95/14921 | 6/1995 | WIPO | C12Q 1/68 |
| WO 95/14922 | 6/1995 | WIPO | C12Q 1/68 |

*Primary Examiner*—Jill Warden
*Assistant Examiner*—Alex Noguerola
*Attorney, Agent, or Firm*—Paul D. Grossman

[57] ABSTRACT

An electrophoretic method for purifying a nucleic acid sample is disclosed. The method generally comprises the steps of (1) providing a nucleic acid sample comprising a desired nucleic acid and one or more contaminants, (2) providing an electrophoresis matrix having a loading well and a recovery well formed therein, (3) placing the nucleic acid sample into the loading well, (4) performing a first electrophoresis comprising electrophoresing the nucleic acid sample for a first time effective to transport the desired nucleic acid out of the loading well and into the electrophoresis matrix; and (5) performing a second electrophoresis comprising electrophoresing the nucleic acid sample for a second time effective to transport the desired nucleic acid out of the electrophoresis matrix and into the recovery well. According to the method, the first and second electrophoresis steps are effective to substantially reduce the concentration of contaminants relative to the concentration of desired nucleic acid in the nucleic acid sample, thereby producing a purified nucleic acid. In the method, the loading and recovery wells may be the same or different, and the electric fields may be DC or alternating. Also disclosed is a preparative electrophoresis method employing an alternating electrical field.

16 Claims, 5 Drawing Sheets

ELECTROPHORETIC NUCLEIC ACID PURIFICATION METHOD

FIELD OF THE INVENTION

This invention relates to the field of electrophoresis. More specifically, this invention relates to electrophoretic methods and apparatus useful for the purification of nucleic acids.

BACKGROUND

Analysis of nucleic acid structure has become the focus of much of modem biology, biotechnology and medicine. Modem nucleic acid analysis techniques such as PCR, fragment-length-polymorphism analysis, and DNA sequencing provide information useful for a variety of applications including diagnosis of disease, organism identification, and tracking evolutionary relatedness. A necessary preliminary step in any nucleic acid analysis method is the preparation of nucleic acid which is free from contaminants which can interfere with enzymes used in these techniques, e.g., contaminants which can inactivate polymerase enzymes used in PCR and DNA sequencing methods.

A wide variety of nucleic acid purification techniques are available based on a range of different physical and chemical principles. The most common nucleic acid purification methods include organic/aqueous liquid—liquid extraction, solid-phase adsorption, precipitation, density-gradient centrifugation, and preparative electrophoresis. Electrophoretic methods are particularly attractive because they result in nucleic acid having a high purity and a large molecular weight.

But, conventional preparative electrophoretic methods suffer from significant shortcomings which limit their practical utility, particularly in the context of high-throughput applications. A particularly problematic aspect of conventional preparative electrophoretic methods is the manner in which a purified nucleic acid is removed from an electrophoresis medium, e.g., an electrophoresis gel. In one class of sample removal processes, the purified nucleic acid is manually excised from the electrophoresis gel. These sample-excision methods are disadvantageous because the nucleic acid and gel material must be separated after excision of the sample band, the procedure requires significant manual intervention, and the purified nucleic acid must be visualized prior to excision in order to locate the desired sample band. In a second class of sample removal techniques, the purified sample is eluted off of the electrophoresis gel into a gel-free buffer. However, such elution methods require that multiple fractions be collected, the purified sample band be visualized, and/or the elution properties of the desired nucleic acid be known.

SUMMARY

The present invention is directed towards the discovery of a class of novel preparative electrophoresis methods useful for the purification of nucleic acids. The methods are particularly useful for the preparation of nucleic acid samples prior to treatment with enzymes, e.g., in Sanger-type sequencing, oligonucleotide ligation assays, and PCR.

In a first aspect, the invention comprises a method for purifying a nucleic acid sample comprising the steps of (1) providing a nucleic acid sample comprising a desired nucleic acid and one or more contaminants, (2) providing an electrophoresis matrix having a loading well and a recovery well formed therein, placing the nucleic acid sample into the loading well, (3) performing a first electrophoresis comprising electrophoresing the nucleic acid sample for a first time effective to transport the desired nucleic acid out of the loading well and into the electrophoresis matrix, (4) performing a second electrophoresis comprising electrophoresing the nucleic acid sample for a second time effective to transport the desired nucleic acid out of the electrophoresis matrix and into the recovery well, (5) wherein the first and second electrophoresis is effective to substantially reduce the concentration of contaminants relative the concentration of desired nucleic acid, thereby producing a purified nucleic acid. In the method, the loading well and the recovery well may be the same well or different wells.

In a first preferred embodiment of this first aspect of the invention, referred to herein as the "trap mode" of the invention, the loading well and the recovery well are spatially overlapping wells, and the electrophoresis matrix comprises a bulk portion and a well-matrix-interface portion, and the matrix is effective to trap the desired nucleic acid in the well-matrix-interface portion such that the desired nucleic acid is substantially prevented from entering the bulk portion of the matrix.

In a second preferred embodiment of the first aspect, referred to herein as the "contaminant-dilution mode" of the invention, the loading well and the recovery well are spatially overlapping wells, and the first electrophoresis is sufficient to transport a portion of the contaminants out of the loading well, through the electrophoresis matrix, and into a contaminant dilution reservoir, the reservoir containing a volume of buffer sufficient to substantially dilute the contaminants entering the reservoir.

In a third embodiment of the first aspect of the invention, referred to herein as the "LITAC-reverse-field mode", the loading well and the recovery well are spatially overlapping wells, the first electrophoresis employs a DC electrical field and the second electrophoresis employs a LITAC electrical field.

In a fourth preferred embodiment of the first aspect present invention, the loading and recovery wells are spatially distinct, and the first electrophoresis employs a DC electrical field and the second electrophoresis employs a LITAC electrical field.

In a fifth preferred embodiment of the first aspect present invention, the loading and recovery wells are spatially distinct, and the first electrophoresis comprises electrophoresing the desired nucleic acid in a first direction and the second electrophoresis comprises electrophoresing the desired nucleic acid in a second direction different from the first direction.

In a second aspect, the present invention consists of a method for the electrophoresis of a nucleic acid sample located in an electrophoresis matrix comprising subjecting the nucleic acid sample to a LITAC electrical field comprising a forward electrical field $E_F$ and a reverse electrical field $E_R$.

In a third aspect, the present invention comprises a method for the electrophoresis of a nucleic acid sample located in an electrophoresis matrix comprising subjecting the nucleic acid sample to a ZIVE electrical field comprising a forward electrical field $E_F$ and a reverse electrical field $E_R$.

Various aspects and/or embodiments of the above-described invention achieve one or more of the following important advantages over known electrophoretic purification methods: (1) using the methods of the invention, there is no need to physically remove sample bands from an electrophoresis gel subsequent to electrophoretic separation—instead, the purified sample is located in a gel-free recovery well and is dissolved in a buffer suitable for subsequent enzymatic treatment, thereby greatly facilitating the automation of post-purification sample recovery; (2) using the methods of the invention, there is no need to collect multiple fractions resulting from a post-electrophoresis elution process—instead, the purified sample is located in a gel-free recovery well and is dissolved in a buffer suitable for subsequent enzymatic treatment, thereby reducing the amount of sample dilution, eliminating the need to collect multiple fractions, and eliminating the requirement for a priori knowledge of the migration behavior of a desired nucleic acid; (3) using the methods of the invention, there is no need to visualize the desired nucleic acid subsequent to electrophoretic separation in order to effect its recovery—instead, subsequent to electrophoresis, the purified sample is located in a gel-free recovery well; (4) using the methods of the invention, there is no need to separate an electrophoresis matrix from a purified nucleic acid; and, (5) using the methods of the invention, nucleic acid is purified to a sufficient purity to allow for efficient PCR amplification in a single step without the need to perform centrifugation or ethanol precipitation to concentrate the purified nucleic acid.

These and other features and advantages of the present invention will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the methods of the present invention effect the separation of a nucleic acid sample into two fractions: a first fraction comprising nucleic acid molecules smaller than a critical size, M*, and contaminants which interfere with enzymatic treatment of a purified nucleic acid, and a second fraction comprising nucleic acid molecules larger than M*, such molecules being referred to herein as a "desired nucleic acid".

The methods of the invention generally comprise the following six method steps: (1) providing a nucleic acid sample comprising a desired nucleic acid and one or more contaminants; (2) providing an electrophoresis matrix having a loading well and a recovery well formed therein, wherein the loading and recovery wells may be the same well or different wells; (3) placing the nucleic acid sample into the loading well; (4) performing a first electrophoresis wherein the nucleic acid sample is electrophoresed for a first time effective to transport the desired nucleic acid out of the loading well; (5) performing a second electrophoresis wherein the nucleic acid sample is electrophoresed for a second time effective to transport the desired nucleic acid into the recovery well; and (6) removing the purified nucleic acid from the recovery well. The first and second electrophoresis steps are effective to substantially reduce the concentration of contaminants relative the concentration of desired nucleic acid in the nucleic acid sample, thereby producing a purified nucleic acid.

For ease of discussion, the methods of the invention are divided into two categories: single-well methods in which the loading well and the recovery well are the same well, and multi-well methods, in which the loading and recovery wells are spatially distinct.

I. General Considerations

A. Nucleic Acid Sample

The nucleic acid sample of the invention may be derived from any living or dead biological organism. Exemplary sources of sample nucleic acid include but are not limited to cells, microorganisms, tissue, blood, and viruses.

The nucleic acid sample of the invention generally comprises three components: (1) a desired nucleic acid, (2) one or more nucleic acid contaminants, and (3) one or more non-nucleic acid contaminants. The desired nucleic acid is characterized by having a size which is greater than a critical size, M*, where the magnitude of M* is a function of a number of experimental parameters including the concentration and nature of the electrophoresis matrix, the type and magnitude of electric field used, and buffer composition and ionic strength. In practice, M* is typically smaller than about 20 kbp.

Conversely, nucleic acid contaminants are nucleic acid molecules, e.g., RNA or DNA, characterized by having a size less than the critical size M*.

Non-nucleic acid contaminants comprise any species that is capable of interfering with post-purification enzymatic treatment of the desired nucleic acid, e.g., treatment with a polymerase, a ligase, or other enzymes which utilize a nucleic acid substrate. Exemplary contaminants include but are not limited to proteins, peptides, high-concentration salts, and heme.

Many times, prior to subjecting a nucleic acid sample to the purification methods of the invention, it is necessary to isolate the nucleic acid from a nucleic-acid-containing starting material. Such starting materials may take a variety of forms including but not limited to 20-million-year-old fossilized plants, human remains, hair, paraffin-embedded biopsy specimens, amber-encrusted insects, cells, blood, and tissue specimens, and the like. Preferably, the starting material is whole blood. Clearly, such diverse starting materials each place unique constraints and requirements on the method used for nucleic acid isolation. However, generally, such isolation procedures must at least serve to substantially remove any particulate contaminants from the nucleic acid sample and substantially solubilize the nucleic acid sample.

Generally, suitable isolation procedures include disruption of cells by mechanical or chemical means followed by treatment with proteolytic enzymes to digest proteins or break down other cellular macrostructures. For example, to isolate a nucleic acid sample from blood, two types of extraction approaches have been used: "complex" methods based on extensive DNA purification, and "simple" methods that require less sample manipulations.

"Complex methods" are generally based on proteinase K digestion or protein salting-out, followed by chlorophorm/ phenol extraction (or DNA adsorption to silica particles) by ethanol or isopropanol precipitation (Molecular Cloning: A Laboratory Manual, Second Edition, Sambrook et al. eds., CSH Press (1989)). Such protocols usually provide high yields of relatively pure DNA. However, such methods typically require a relatively large sample size, e.g., 10 ml of blood, employ toxic, volitile and/or explosive reagents, e.g., phenol and chloroform, and are based on relatively time-consuming and laborious protocols that are difficult to automate. The extensive sample manipulation required also increases the potential for contamination and DNA shearing. In some cases, white blood cells or nuclear isolation steps are required to minimize PCR inhibition. These steps are usually arduous when less than 300 $\mu$l of blood are available for extraction, as the pellet size is small and difficult to efficiently isolate form the supernatant. Failed DNA ethanol precipitation can also be experienced. Further, complete solubilization of ethanol-precipitated DNA is time-consuming and difficult to achieve. This difficulty of re-solubilization also applies to protocols that require DNA capture on a solid support, e.g., silica or glass beads, glass fiber discs or resins, and magnetic beads. Common to all DNA support-capture methods is also the potential for template loss due to incomplete capture, retention during washing and desorption.

For the most part, "simple" protocols such as DNA purification by means of magnetic beads, or "boil and go" methods are fast and easy, usually requiring only a 10–50 $\mu$l sample size and minimal manipulation. (Dynabeads DNA Direct Kit from Dynal, Inc.; Walsh et al., *Biotechniques*, 10: 506 (1991).) However, the DNA samples obtained using these methods is typically of low quality, i.e., is character-ized by a relatively low 260/280 absorbence ratio, e.g., 1.2 to 1.4, and low PCR yields, e.g., 10 to 30%. With "boil and go" protocols the temperature required for successful extraction, e.g., above about 95° C., is usually incompatible with the recovery of fragile DNA, e.g., the Fragile X region of the human genome, and causes DNA denaturation. Such denaturation of the purified nucleic acid is problematic if further enzymatic digestion of the purified nucleic acid is desired because single-stranded DNA is not a target for many common restriction endonucleases.

In an important aspect of the present invention, a novel DNA isolation procedure is described that is based on the treatment of whole blood with proteolytic enzymes to digest proteins or break down other cellular macrostructures. This method is particularly attractive because only a low con-centration of proteolytic enzyme is used compared to con-ventional methods thereby eliminating the need to remove the enzyme prior to PCR analysis. Thus, using the method of the invention, there is no need for "heat-kill" treatments, centrifugation and/or precipitation of the nucleic acid sample in order to remove residual enzyme. Further, because no manipulation of the sample is required, largely intact high molecular weight double-stranded DNA may be recovered using the instant method. Because this protocol requires minimal manipulation of the sample and no centrifugation, it is therefore easily amenable to automation.

According to the isolation procedure of the invention, a blood/lysis buffer mixture is formed by mixing 1 volume of fresh blood with 6 volumes of a lysis buffer and 0.4 volumes of a proteinase K solution (e.g., about 20 mg/ml). Preferably, the basis volume of fresh blood is about 10 to 20 $\mu$l. A preferred lysis buffer composition is where 1.4 ml of the lysis buffer consists of 1 ml of 110 mM Tris-HCl (pH 8.3), 250 mM NaCl, 19 mM sarkosyl detergent, 0.05% Nonidet P-40, and 0.4 ml of 2-pyrrolidinone. The blood/lysis buffer mixture is then incubated at about 65° C. for about 35 minutes.

B. Electrophoresis Matrix

The electrophoresis matrix used in the invention may be formed using any one of a number of conventional tech-niques. Generally, the electrophoresis matrix is effective to retard the electrophoretic migration of a desired nucleic acid relative to its migration in a matrix free medium. Moreover, the matrix must impart a differential electrophoretic mobility between the desired nucleic acid and the contaminants. In addition, the integrity of the gel matrix must be maintained at elevated temperatures that may be encountered during electrophoresis. In certain preferred embodiments of the invention, the matrix must also substantially exclude nucleic acids having a size greater than M* and/or impart an electrical-field-dependent electrophoretic mobility to the desired nucleic acid.

The electrophoresis matrix may be formulated in a con-ventional "wet-gel" format or a "dry-gel" format. In a wet gel format, the electrodes used to effect the electrophoresis are located in a buffer reservoir and are submerged in a running buffer, and electrical communication between the electrodes and the matrix is established through the running buffer. In addition, in the wet-gel configuration, a top surface of the matrix is covered with a thin film of running buffer, e.g., at least approximately 5 mm deep.

On the other hand, in a dry-gel format there are no buffer reservoirs. Instead, the electrodes are in direct contact with the matrix. Several alternative dry-gel electrode configura-tions may be used. Exemplary dry-gel electrode configura-tions include a flat sheet of metal, a grid of metal wires, or a series of metal pins which penetrate into the body of the gel. Preferably, the metal used to form the electrodes is platinum or another similarly chemically passive material. Preferably, a buffer-saturated sponge material is disposed between the electrodes and the electrophoresis matrix in order to provide electrical communication between the elec-trodes and the matrix without causing melting of the matrix in the vicinity of the electrode in a way which accommo-dates shrinkage of the matrix, and to serve as a reservoir for electrophoresis buffer. Generally, lower field intensities must be used with a dry gel in order to protect the gel integrity. Indeed, the gel may tend to melt near the electrodes when a high field intensity is used. In addition, the small amount of buffer trapped within the gel is generally not sufficient to stabilise the current and the conductivity during electrophoresis. Ionic depletion is a common phenomenon. As a consequence, the resistance is time-dependent and often depends on the polarity of the field, especially after several minutes. Thick gels, i.e., gels having a thickness of between about 5 and 10 mm, somewhat reduce these prob-lems.

In certain preferred embodiments of the present invention, it is desirable that the matrix cause substantial electroos-motic flow, e.g., greater than $2.0*10^4$ $cm^2$/V s. Such elec-troosmotic flow may serve to sweep contaminants out of a loading well while the desired nucleic acid is retained in the well. Generally, matrices including charged groups will support electroosmotic flow, e.g., certain agarose matrices, e.g., "High EEO" agarose materials supplied by the Sigma Chemical Company.

Exemplary electrophoresis matrices include but are not limited to agarose and crosslinked polyacrylamide. Preferably, the matrix is gelled agarose. More preferably, the agarose is a high-melt agarose having a melting temperature above about 85° C.

Loading and recovery wells are matrix-free regions formed in the electrophoresis matrix that contain a buffer solution. Sample nucleic acid is placed in the loading well prior to purification and a purified nucleic acid is removed from the recovery well subsequent to purification. The loading and recovery wells may be the same well or different wells. Because there is no matrix in the wells, placement of sample nucleic acid and recovery of purified nucleic acid may be accomplished without having to excise the purified nucleic acid from a gel matrix. The shape of the wells is arbitrary, but it is preferred that the wells of the invention have a substantially flat bottom and a substantially flat wall in the direction of electrophoresis, because non-flat bottoms can negatively affect the electric field in proximity to the wells, and non-flat walls in the direction of electrophoresis can adversely affect the shape of a sample band during electrophoresis. Moreover, the depth of the wells should be less than the thickness of the electrophoresis matrix, i.e., the bottom of the wells should be formed by the matrix, not by a matrix-supporting member.

Capillary action may cause the electrophoresis matrix in contact with combs used to form the loading and recovery wells to rise on the combs when the matrix is prepared, e.g., when an agarose gel is poured. This capillary rise may cause the thickness of the gel to be greater between two adjacent wells than in the body of the gel. This increased thickness can cause an electric field to be inhomogeneous in the vicinity of the wells. It was discovered that eliminating this inhomogeneous electric field is important in order to ensure reproducible results and maximum yield of purified nucleic acid. This problem may be solved by using a comb made of a material which does not cause capillary action, or, by trimming any gel protruding around the wells using a razor blade thereby producing a gel with a top surface that is uniformly flat.

The electrophoresis buffer used may be any conventional electrophoresis buffer. Preferably the buffer has a low electrical conductivity, thereby reducing the amount of Joule heating generated during the electrophoresis, and does not detrimentally interact with nucleic acids. In addition, the buffer should be compatible with subsequent enzymatic treatment of the purified nucleic acid, e.g., be compatible with the PCR process. Thus, preferably the recovery-well buffer has a low salt concentration and a low ionic strength, e.g., TAE buffer consisting of 0.04M Tris, 0.04M acetic acid, and 0.002M EDTA.

The electrophoresis matrix may be oriented horizontally or vertically. In the horizontal orientation, the direction of the electrophoresis is in a horizontal direction, while in the vertical orientation, the direction of the electrophoresis is in a vertical direction. Generally, the horizontal orientation is preferred when the wet gel-format is used and in multi-well methods (see below).

In a particularly preferred embodiment of the electrophoresis matrix of the present invention, a matrix is constructed by forming a gel/plastic composite composed of an agar impregnated sintered plastic. These matrices are preferred because they provide enhanced structural integrity as compared to unsupported gel materials.

Exemplary sintered plastics useful; in the gel/plastic composites of the invention are produced by several manufacturers, e.g., Porex Technology, Inc., and GenPore, Inc. Generally, these sintered plastics are characterized by an intricate network of open-celled omnidirectional pores. These pores, which can be made in average pore sizes from 7–250 microns, give the porous plastics its structural strength. Several types of polymers are used in combination to form the sintered plastic, e.g., high-density polyethylene (HDPE), ultra-high molecular weight polyethylene (UHMW), polypropylene (PP), polyvinylidene fluoride (PVDF), polytetrafluoroethylene (PTFE), Nylon 6 (N6), polyethersulfone (PES), and ethyl vinyl acetate (EVA).

To form the composites, a sheet of sintered plastic, e.g., POREX 250 micron pore size polypropylene (12 in.×12 in.×¼ in.), is cut to the desired dimensions, e.g., 3.0 cm long by 11.7 cm wide. Flat bottomed wells are then drilled into the plastic, e.g., approximately 3 mm to 5 mm deep and 5 mm in diameter. The wells should not penetrate through the lower surface of the plastic sheet. Then, to increase the hydrophilicity of the plastic, the porous plastic piece is dipped into a wetting agent, such as 70% ethanol, or treated with a high voltage plasma treatment which introduces hydrophilic groups on the surface of the plastic (—OH, —COOH, or —NH), e.g., as provided by MetroLine Industries Inc. Once the sintered plastic has been treated to render it sufficiently hydrophilic, it is contacted with melted agarose, e.g., placed into boiling agarose (0.8% to 3.0% dissolved in 0.2× TAE buffer). The agarose is allowed to solidify and the solidified agarose attached to the outside surface of the plastic is mechanically trimmed away. The agar impregnated plastic is then placed in an electrophoresis tank and submerged in electrophoresis buffer, e.g., to a depth of 5 mm. Electrophoresis is carried out in the same manner as with non-composite matrices except that the voltage is generally substantially reduced as compared with non-composite matrices.

C. Electrical Fields

The magnitude of the electric field used in the various embodiments of the present invention depends upon a number of factors, however, generally, in order to reduce the time required for sample purification, the maximum possible field strength is used. The value of the maximum field is limited by the ability of the electrophoresis matrix to withstand the elevated temperatures caused by the Joule heating generated during electrophoresis. The amount of Joule heating produced by the electrophoresis is determined by a number of factors including the thickness of the electrophoresis matrix, the ionic strength and electrical conductivity of the electrophoresis buffer, the electric field strength, and the ionic strength and electrical conductivity of the nucleic acid sample. The value of the minimum field is limited by the ability of the field to transport the contaminants and/or the desired nucleic acid out of and/or into the loading well. Preferably, electric fields of between 5 and 15 V/cm are used in the present invention.

In certain embodiments of the present invention, time-dependent electrical fields are used to enhance the differential migration between a desired nucleic acid and contaminants and the efficient recovery of a purified nucleic acid. A first type of time-dependent electrical field is referred to herein as a liquid-trapping-alternating-current field, or "LITAC" field. Under the influence of a LITAC field, a desired nucleic acid has a finite forward velocity in an electrophoresis matrix, but, has a zero net velocity in free solution, i.e., in the loading and recovery wells. In addition, under the influence of a LITAC electric field, the contaminants have a zero net velocity in both the matrix and in free solution. This property of LITAC-induced migration serves several useful purposes which will be described in detail below.

Generally, a LITAC field is characterized by a forward time $t_F$, a forward electrical field $E_F$, a reverse time $t_R$, and a reverse electrical field $E_R$. More specifically, a LITAC field is specified by the following relationships between $t_F$, $E_F$, $t_R$ and $E_R$: (1) the product of the forward time and the forward electrical field is equal to the product of the reverse time and the reverse electrical field, i.e., $$t_F{}^*E_F = t_R{}^*E_R;$$

(2) the forward electrical field is greater than the reverse electrical field; and (3) times $t_F$ and $t_R$ are chosen such that each is less than the time required for the desired nucleic acid to transit a recovery well, e.g., about 30 sec, and greater then the reorientation time of the desired nucleic acid, e.g., about 1 sec. Preferably, $E_F/E_R$ is between about 2 and 3, and more preferably, the ratio is approximately 2.4. In order to speed up the process, the value of $E_F$ is chosen to be the maximum electrical field which is compatible with the electrophoresis system, i.e., the maximum field which does not melt or otherwise decompose the gel matrix.

A second type of time-dependent electrical field useful in the context of the present invention is referred to herein as a zero-integrated-velocity-electrophoresis field, or ZIVE. In contrast to a LITAC field, under the influence of a ZIVE field, in the electrophoresis matrix, the desired nucleic acid has a zero net migration velocity while the contaminants have a finite forward net velocity.

Generally, a ZIVE field is characterized by a forward time $t_F$, a forward electrical field $E_F$, a reverse time $t_R$, a reverse electrical field $E_R$, a forward electrophoretic velocity under the influence of the forward electrical field $V_F$, and a reverse electrophoretic velocity under the influence of the reverse electrical field, $V_R$. More specifically, a ZIVE field is specified by the following relationships between $t_F$, $E_F$, $t_R$, $E_R$, $V_F$ and $V_R$: (1) the product of the forward time and the forward velocity is equal to the product of the reverse time and the reverse velocity, i.e., $$t_F{}^*V_F = t_F{}^*V_R;$$

(2) the forward electrical field is set at a maximum value as described above for the LITAC field; (3) the reverse electric field is less than the forward electrical field, where $E_F/E_R$ is preferably between about 2 and 3, and more preferably, about 2.4; (4) $t_F$ is selected to be greater than the reorientation time of the desired nucleic acid, and less than the time in which the desired nucleic acid would migrate out of the matrix. Preferably, the forward time is greater than about 5 sec, and more preferably between about 5 sec and 5 min.

II. Purification Methods

A. Single-Well Methods

Single well methods according to the present invention are characterized by a loading well and a recovery well which are the same well, i.e., the nucleic acid sample is loaded into the same well from which the purified nucleic acid is removed. Single-well methods have several advantages over multi-well methods including the following: (1) large genomic nucleic acid which does not normally enter the electrophoresis medium may be recovered, (2) the purified sample does not need to intercept a second well, and (3) more samples can be processed in a given amount of electrophoresis medium because only a single well per sample is required. However, a significant disadvantage of single-well methods is that non-mobile contaminants, e.g., neutral contaminants and large aggregates, can not be separated from the desired nucleic acid.

Contaminant-Dilution Mode. A first single-well method referred to herein as the "contaminant dilution mode" is schematically depicted in FIGS. 1A–E. In this embodiment, a sample nucleic acid is subjected to a first electrophoresis under the influence of a first DC electric field having a magnitude $E_1$ applied for a time $t_1$. This first electrophoresis is sufficient to transport a desired nucleic acid 30 having a critical size greater than M* a distance less than L*, and to transport the mobile contaminants 5 out of a loading/recovery (L/R) well 10, through an electrophoresis matrix 15, and into a contaminant dilution reservoir 20. See FIGS. 1A–D. Once a selected portion of the mobile contaminants have been run out of the matrix into the contaminant dilution reservoir and thereby diluted 25, the sample nucleic acid is subjected to a second electrophoresis under the influence of a second DC electric field having a magnitude $E_2$ applied for a time $t_2$, where $E_1$ and $E_2$ may be the same or different. This second electrophoresis is sufficient to transport the desired nucleic acid 30 back into the L/R well 10. See FIGS. 1D–E.

The contaminant dilution reservoir contains a volume of buffer sufficient to substantially dilute the contaminants entering the reservoir relative to their concentration in the nucleic acid sample. Preferably, the contaminant dilution reservoir is an electrode buffer reservoir containing a buffer volume equal to at least six times the volume of the electrophoresis matrix.

To facilitate recovery of the desired nucleic acid, the second reverse electric field typically has the same magnitude and duration, but opposite polarity as the first forward electric field. Furthermore, by adjusting the time of the first electrophoresis, the degree of purity and the recovery efficiency of the desired nucleic acid may be modulated. That is, a longer $t_1$ will generally result in increased purity of desired nucleic acid, but provide a decreased recovery efficiency. Preferably, according to this embodiment of the invention, the first and second electric fields are DC fields having a field strength of approximately 10 to 12 V/cm.

Trap Mode. A second single-well method referred to herein as the "trap mode" is schematically depicted in FIGS. 2A–D. This mode requires an electrophoresis matrix which comprises a bulk region and a well-matrix-interface region, wherein the well-matrix-interface region is effective to trap a desired nucleic acid thereby preventing such nucleic acid from entering the bulk region of the matrix. Such a matrix may be formed using a high concentration of matrix polymer, e.g., 30 mg/mL agarose.

In this embodiment, the sample nucleic acid is subjected to a first electrophoresis under the influence of a first DC electric field having a magnitude $E_1$ applied for a time $t_1$. This first electrophoresis is sufficient to transport the mobile contaminants 5 out of a L/R well 10 and into an electrophoresis matrix 15, and transport the desired nucleic acid 30 out of the L/R well and into the well-matrix-interface region of the matrix. See FIGS. 2A–B. Once the contaminants have been transported out of the L/R well and into the electrophoresis matrix, several alternatives exist for returning the desired nucleic acid back to the L/R well.

In a first alternative, the desired nucleic acid is removed from the L/R well 10 after completion of the first electrophoresis without any further electrophoresis steps. According to this alternative, the desired nucleic acid is recovered from the well-matrix-interface region by simple diffusion and/or by gentle agitation of the buffer located in the L/R well. See FIG. 2C.

In a second alternative, the desired nucleic acid is removed from the interface region and returned to the L/R well 10 by subjecting the sample nucleic acid to a second electrophoresis under the influence of a second DC electric field having a magnitude $E_2$ applied for a time $t_2$, where $t_2 \ll t_1$. See FIG. 2D. The time $t_2$ must be significantly shorter than the time $t_1$ for two reasons. First, if $t_2$ is too long, the desired nucleic acid will be transported out of the interface region, across the L/R well, and into the opposite wall of the L/R well, thereby making the desired nucleic acid unavailable for subsequent recovery. Second, if $t_2$ is too long, the contaminants will be transported back into the L/R well, thereby re-contaminating the desired nucleic acid. For example, $t_1$ is typically approximately 15 to 30 min while $t_2$ is approximately 30 sec.

Figure 1A:
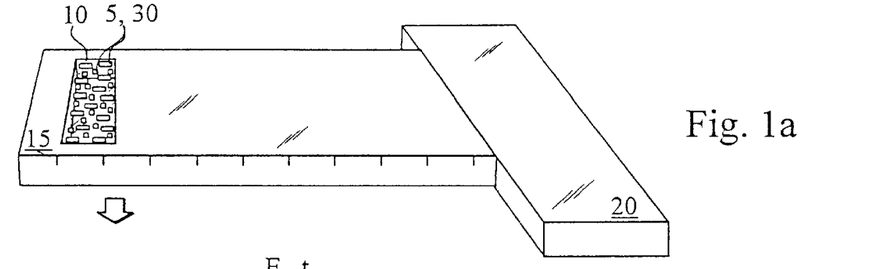
FIGS. 1A–1E show a schematic depiction of the contaminant-dilution embodiment of the invention.
Figure 1B:
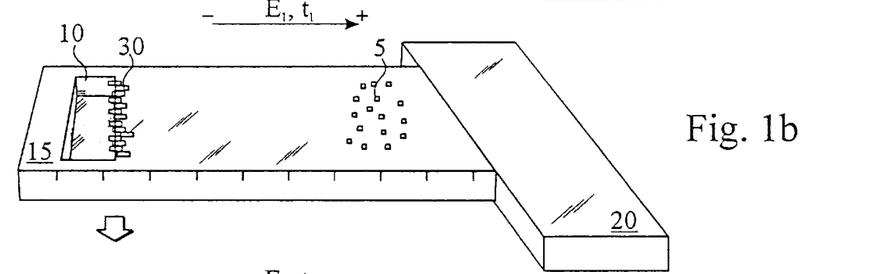
Figure 1C:
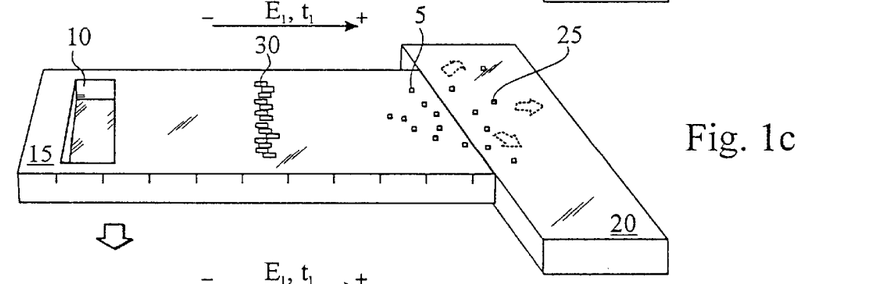
Figure 1D:
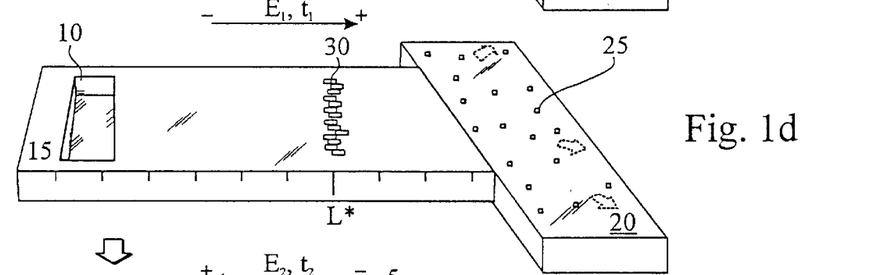
Figure 1E:
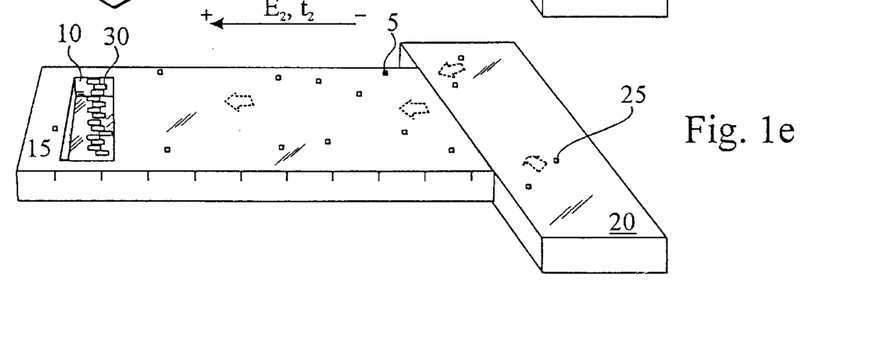
Figure 2A:
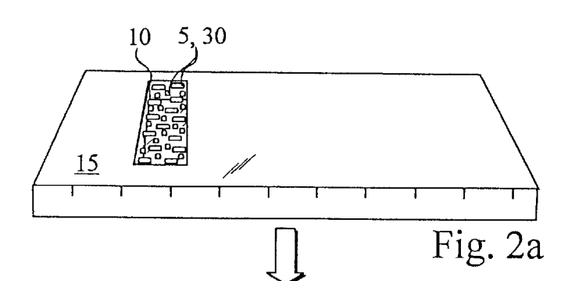
FIGS. 2A–2D show a schematic depiction of a trap embodiment of the invention.
Figure 2B:
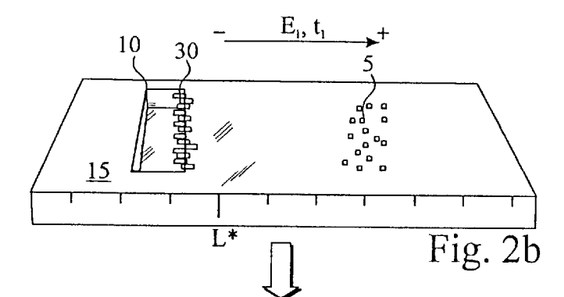
Figure 2C:
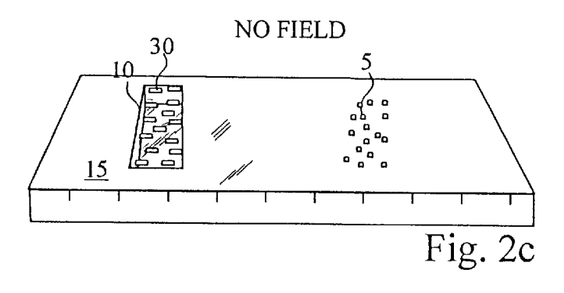
Figure 2D:
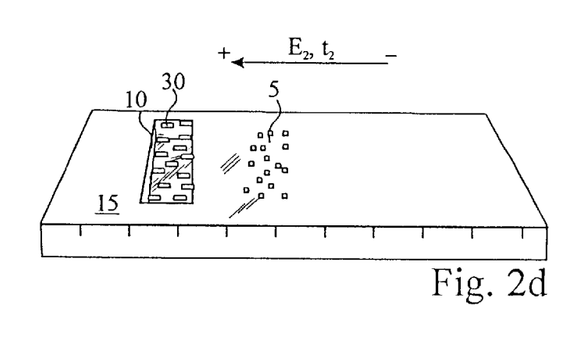
Figure 2E:
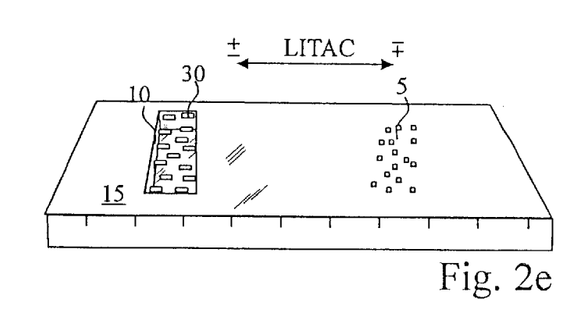

In a variant of the second alternative embodiment of the trap mode of the present invention, part or all of the first and/or second electrophoresis is performed using a LITAC field rather than a DC field. Using a LITAC field to transport the desired nucleic acid back into the L/R well provides several advantages including the following: (1) the mobile contaminants can not return to the L/R well under the influence of the LITAC field, and (2) the desired nucleic acid can not migrate out of the L/R well once it has returned to the well. In a preferred embodiment, the first electrophoresis employs an exclusively DC field, and the reverse electrophoresis employs both DC and LITAC fields.

Figure 3A:
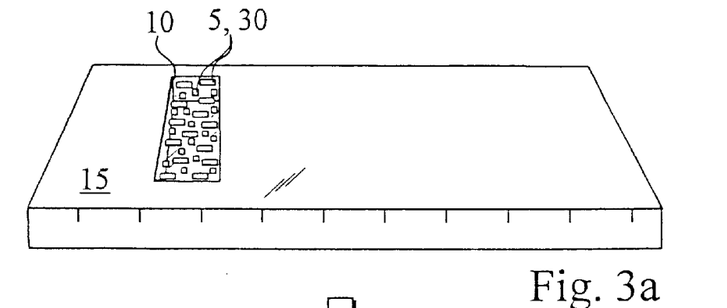
FIGS. 3A–3C show a schematic depiction of a LITAC reverse field embodiment of the invention.
Figure 3B:
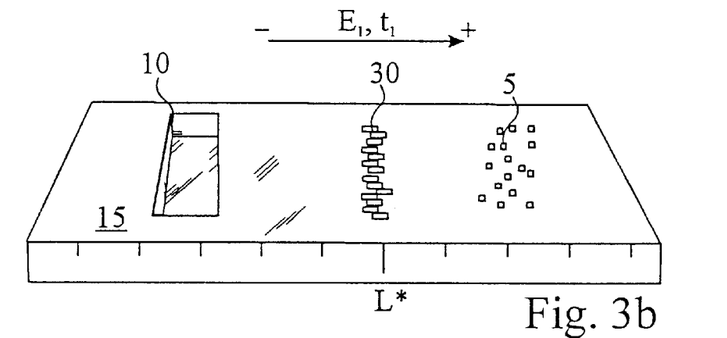
Figure 3C:
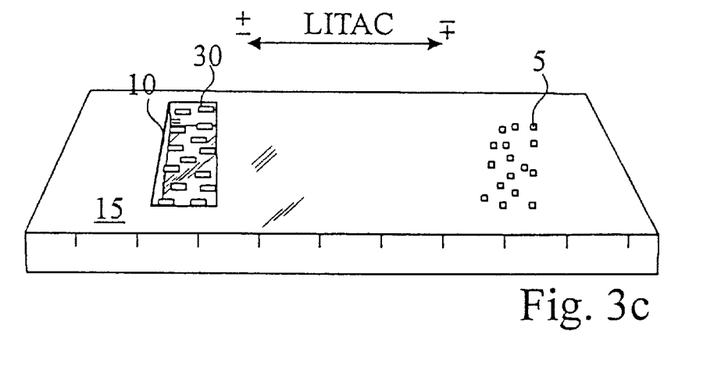
Figure 4A:
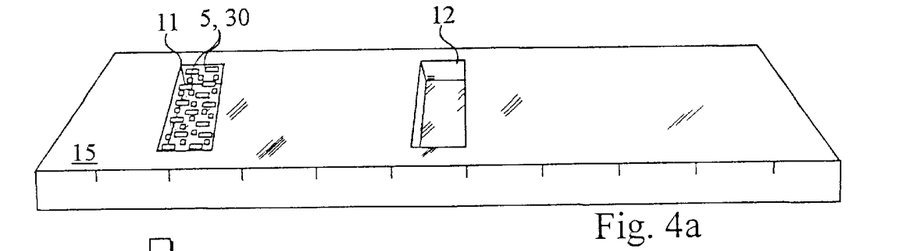
FIGS. 4A–4D show a schematic depiction of a single direction multi-well embodiment of the invention.
Figure 4B:
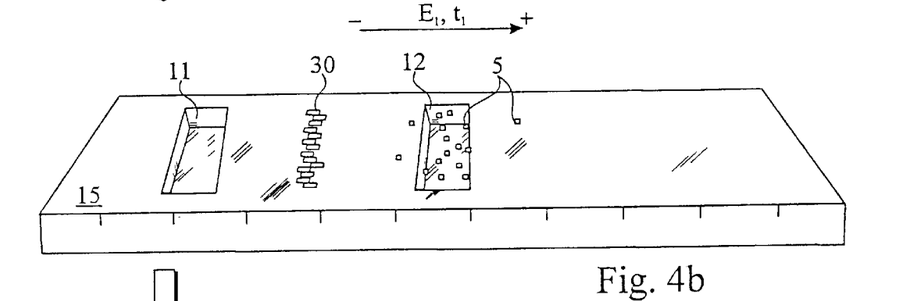
Figure 4C:
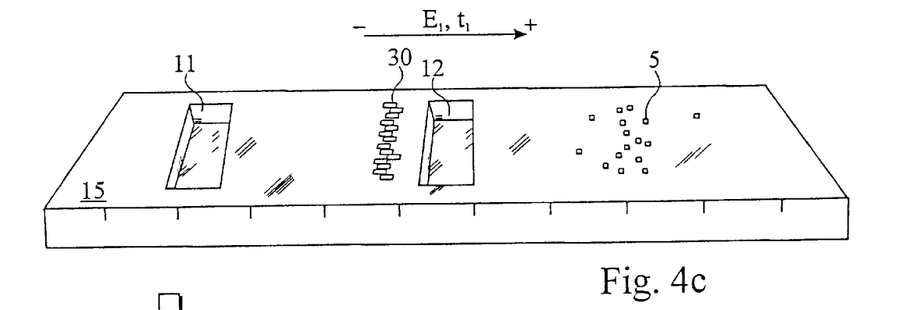
Figure 4D:
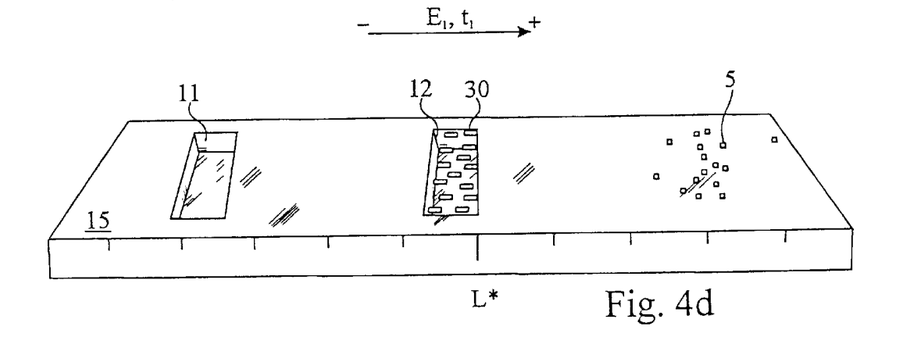
Figure 5A:
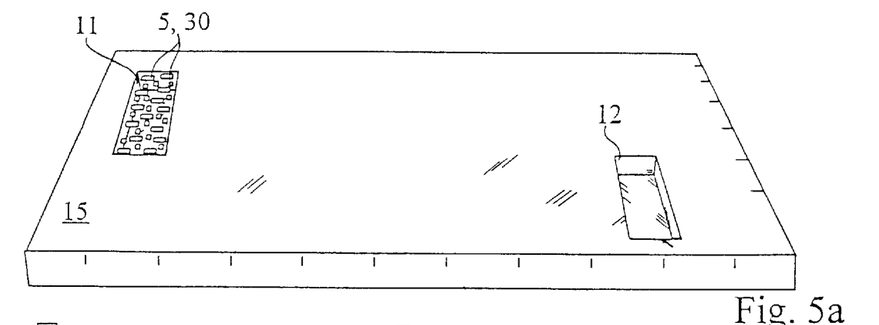
FIGS. 5A–5D show a schematic depiction of a multi-direction multi-well embodiment of the invention.
Figure 5B:
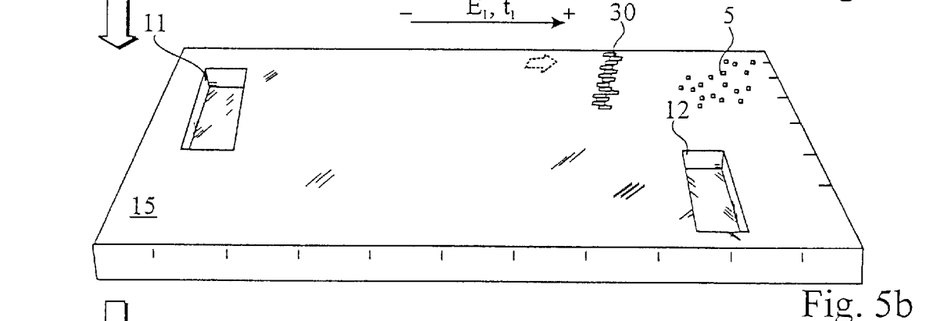
Figure 5C:
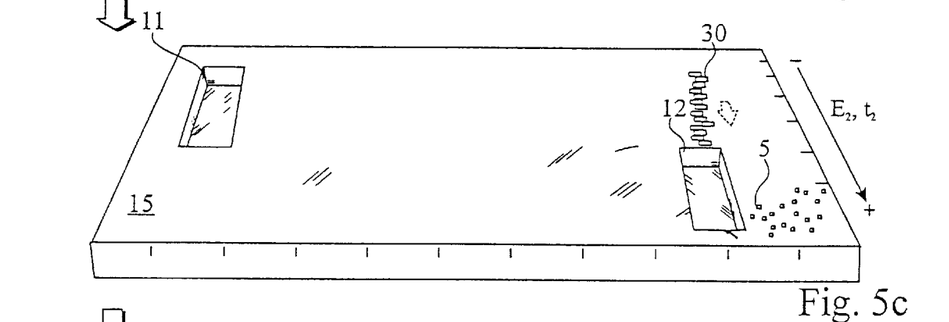
Figure 5D:
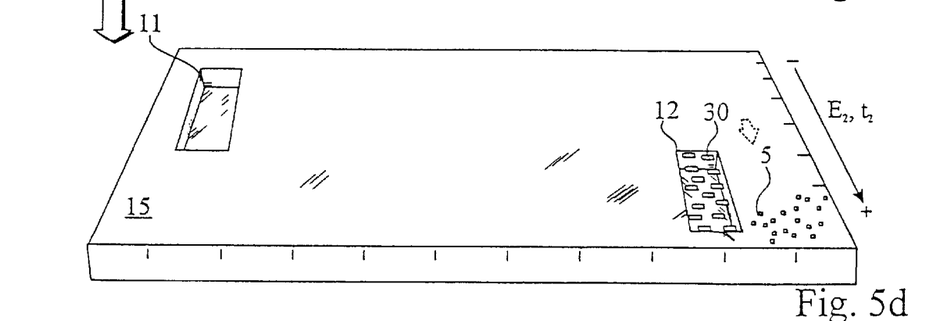

LITAC Reverse Field Mode. A third single-well method referred to herein as the "LITAC reverse field mode" is schematically depicted in FIGS. 3A–C. In this mode, the sample nucleic acid is subjected to a first electrophoresis under the influence of a first DC electric field having a magnitude $E_1$ applied for a time $t_1$. This first electrophoresis is sufficient to transport the desired nucleic acid 30 and the mobile contaminants 5 out of a L/R well 10 and into an electrophoresis matrix 15. See FIGS. 3A–B. Once the desired nucleic acid and contaminants have been transported into the electrophoresis matrix, the sample nucleic acid is subjected to a second electrophoresis under the influence of a LITAC electric field sufficient to return the desired nucleic acid 30 back to the L/R well 10 and immobilize the contaminants in the matrix. See FIGS. 3B and C.

C. Multi-Well Methods

Multi-well methods according to the present invention are characterized by a loading well and a recovery well which are spatially distinct, i.e., the nucleic acid sample is loaded into a different well from that which the purified nucleic acid is removed. Multi-well methods have the advantage that the desired nucleic acid may be separated from non-mobile contaminants, i.e., neutral contaminants or large aggregates. However, multi-well methods suffer from several drawbacks including the following: (1) large genomic nucleic acid which does not enter the electrophoresis medium can not be recovered, (2) the electrophoretic trajectory of the desired nucleic acid must be carefully controlled so that the purified nucleic acid intercepts a recovery well, and (3) fewer samples can be processed in a given area of electrophoresis medium because multiple wells per sample are required.

Single-Direction Multi-Well Mode. A first multi-well method referred to herein as the "single-direction multi-well mode" is schematically depicted in FIGS. 4A–D. In this embodiment, the sample nucleic acid is subjected to a first electrophoresis under the influence of a first DC electric field having a magnitude $E_1$ applied for a time $t_1$. This first electrophoresis is sufficient to transport the desired nucleic acid 30 and the mobile contaminants 5 out of a loading well 11 and through an electrophoresis matrix 15. See FIGS. 4A–C. The duration of the first electrophoresis is selected to be sufficient to transport the contaminants through the recovery well 12 to a location past the recovery well 12 and transport the desired nucleic acid into or near the recovery well 12. See FIGS. 4C–D. The placement of the desired nucleic acid in the recovery well may be effected using one of two methods. In a first method, the desired nucleic acid is placed in the recovery well by knowing the migration velocity of the desired nucleic acid and the distance between the loading and recovery wells, and adjusting the migration time so as to cause the desired nucleic acid to be located in the recovery well after the first electrophoresis. This "timing-based" method is less preferred because it requires prior knowledge of the migration properties of the desired nucleic acid under the particular experimental conditions. In a more preferred method for recovering the desired nucleic acid in a recovery well, once the contaminants have passed through the recovery well, a LITAC field is used to transport the desired nucleic acid from a position between the loading and recovery wells into the recovery well. By using a LITAC field during this step, the desired nucleic acid will be transported to the recovery well and remain in the recovery well indefinitely.

Multi-Direction Multi-Well Mode. A second multi-well method referred to herein as the "multi-direction multi-well mode" is schematically depicted in FIGS. 5A–D. In certain situations, the multi-direction multi-well mode is preferred over the single-direction multi-well mode because in the former mode the mobile contaminants are not passed through the recovery well. In this embodiment, the nucleic acid sample is subjected to a first electrophoresis under the influence of a first DC electric field having a magnitude $E_1$ applied for a time $t_1$. This first electrophoresis is sufficient to transport the desired nucleic acid 30 and a substantial portion of the mobile contaminants 5 out of a loading well 11, and through an electrophoresis matrix 15. The desired nucleic acid is transported to an intermediate location which is aligned with a recovery well 12. Next, the nucleic acid sample is subjected to a second electrophoresis sufficient to transport the desired nucleic acid into or near the recovery well 12. The desired nucleic acid is then placed in the recovery well using either the timing method or a LITAC field, as described above.

III. EXAMPLES

The invention will be further clarified by a consideration of the following examples, which are intended to be purely exemplary of the invention and not to in any way limit its scope.

Example 1

Purification of λ DNA by Contaminant Dilution Preparative Electrophoresis

Nucleic Acid Sample.

The nucleic acid to be purified consisted of undigested λDNA (48.5 kb long) and DNA fragments obtained after digesting the λDNA with the HindIII restriction enzyme, i.e., fragments 0.6, 2.0, 2.3, 4.4, 6.6, 9.4 and 32.1 kb long. The nucleic acid sample subjected to electrophoresis (total volume of 40 μL) was prepared by mixing 20 μL (1.66 μg) of the HindIII digested λDNA, 10 μL (0.42 μg) of undigested λDNA, and 11 μL of water.

Electrophoresis Apparatus and Conditions.

The electrophoresis was performed in a horizontal orientation. The electrophoresis matrix used was a 0.8% agarose gel made with Molecular Biology grade agarose sold by Promega. The gel was 3.0 cm long and 11.7 cm wide. Each was situated about 1 cm from the top edge of the gel, thereby providing 2.0 cm of gel in the direction of electrophoresis. The wells were spaced approximately 2.5 mm apart. Both the gel and tank buffer were 0.2× TAE, where 1× TAE is 0.04M Tris, 0.04M acetic acid, and 0.002M EDTA. The wells were 5 mm deep, 1 mm wide, and 3.8 mm long.

Electrophoresis was performed in a 27.2×12 cm wide H5 gel electrophoresis tank (Gibco BRL, Life Technologies). Both the forward and reverse electric fields had a magnitude of 10.6V/cm. The electric field across the gel and the temperature of the tank buffer were monitored using a Model 2706 multimeter (BK Precision, Chicago, Ill.). 864 mL of buffer was added to the tank, an amount sufficient to submerge the gel under a 5 mm layer of buffer.

Electrophoresis Protocol.

The nucleic acid sample prepared above was loaded into a loading/recovery well and forward electrophoresis was performed for a period of 28 minutes. The electric field was then turned off and a 120 µL sample was withdrawn from the loading/recovery well (sample time of 0 minute reverse field). Next, the electric field was reversed and 120 µL samples were collected from the loading/recovery well every 1 minute thereafter (without turning the electric field off) for the next 27 minutes resulting in the collection of a total of 28 samples. (The fact that 120 µL samples were collected from a well initially containing only 40 µL of sample was due to the fact that the gel was covered by 5 mm of buffer and that a larger amount of liquid had to be collected from the well in order to insure that most of the DNA present in the well at a given time was collected.) 20 µL of each of 27 collected samples (corresponding to samples collected 1 to 27 minutes of reverse electrophoresis) was then subjected to analytical electrophoresis in order to determine the quantity and size of the purified nucleic acid.

The analytical electrophoresis showed that the sample collected at t=0 contained a relatively large amount of undigested 48.5 kb DNA (estimated concentration of roughly 9 µg/mL) while the sample collected at t=1 minute contained roughly five times more of the 48.5 kb DNA fragment. In contrast, the sample collected after 2 minutes contained roughly 50% less of the 48.5 kb fragment then the sample collected after 1 minute. The samples collected at times 2 to 18 minutes each contained small but increasing amounts of the 48.5 kb DNA fragment. The sample collected after 19 minutes also contained a small amount of the 23.1 kb DNA fragment as well as very small amounts of the 9.4, 6.6, and 4.4 kb DNA fragments. The amount of these four smaller DNA fragments progressively increased from the sample taken at 19 minutes to the sample taken at 24 minutes, was highest in the sample taken at 24 minutes, was slightly reduced in the sample taken at 25 minutes, was further reduced in the sample taken at 26 minutes, and was practically undetectable in the sample taken at 27 minutes. Based on a visual examination of the gel (i.e., by comparing the relative intensity of the sample taken at 24 minutes with the λDNA standard loaded in this gel), it was estimated that the sample taken at 24 minutes represented about 25% of the DNA initially loaded onto the gel.

Based on the above experimental findings, several observations can be made. The fact that the 48.5 kb fragment was observed in the t=0 sample is an indication that some 48.5 kb DNA fragment had not entered the gel even after 28 minutes of forward electrophoresis. The fact that a larger amount of the 48.5 kb fragment was observed in the sample collected after 1 minute of reverse electrophoresis indicates that a relatively large fraction of the 48.5 kb DNA fragment had barely entered the gel after 28 minutes of forward electrophoresis, while 1 minute of reverse electrophoresis was sufficient to return this DNA into the loading/recovery well. The fact that a small (and increasing) amount of the 48.5 kb fragment was observed in samples taken after 2 to 18 minutes of reverse electrophoresis is an indication that DNA that had entered the gel to different extents. The fact that DNA fragments smaller that 4.4 kb (i.e., the 2.2 and 2.0 kb fragments) were never observed is likely due to the fact that they were eluted from the gel into the sample dilution volume, i.e., into the buffer-filled electrode reservoir. The fact that the DNA fragments exhibited a different electrophoretic mobility in the forward and reverse directions, i.e., the fragments that migrated forward for 28 minutes took less than 28 minutes to return to the original well, indicates that the temperature of the gel increased during the electrophoresis (Joule effect).

Example 2

Purification of λ DNA by Multi-Direction Multi-Well Preparative Electrophoresis

Nucleic Acid Sample.

The nucleic acid sample was the same as that described in Example 1 above.

Electrophoresis Apparatus and Conditions.

The electrophoresis was performed in a horizontal orientation. The electrophoresis matrix used was an 0.8% agarose gel made with Molecular Biology grade agarose sold by Promega. The gel was 3.5 cm long and 11.7 cm wide and was supported by a 11.7×1.7 cm tray. In order to allow electrophoresis in multiple directions, the tray had no side members. Instead, the gel tray included one electrode post at each of its four corners. In order to prevent fouling of the electrode posts by the agarose gel, masking tape was wrapped around these four posts during the preparation of the gel, and the tape was removed prior to electrophoresis. The loading well was rectangular in shape, was 2 mm deep and 4 mm wide, and was located approximately 1 cm from the top edge of the gel. The recovery well was also rectangular in shape, and was 5.3 mm thick and 3 mm wide. The recovery well was located 6 mm in front of the starting well, and 2.3 mm to the left of the starting well (when one looks at the gel with the wells on top). Both the gel and tank buffer were 0.2× TAE.

Electrophoresis was performed in a 27.2×12 cm H5 gel electrophoresis tank (Gibco BRL, Life Technologies). Both the forward and transverse electric fields had a magnitude of 11.5V/cm. The electric field across the gel and the temperature of the tank buffer were monitored using a Model 2706 multimeter (BK Precision, Chicago, Ill.). 870 mL of buffer was added to the tank, an amount sufficient to submerge the gel under a 5 mm layer of buffer.

Electrophoresis Protocol.

The nucleic acid sample was loaded into the loading well and forward electrophoresis was performed for 16 minutes. The electric field was then turned off, the gel was manually rotated by 90°, and the now transverse electric field was turned on. 100 µL samples were collected once every minute (without turning the electric field off) from the recovery well from a time 3 minutes after starting the transverse electric field to time a 10 minutes after starting the transverse electric field. A total of 8 samples were collected. 20 µL of each of the 8 collected samples (corresponding to samples collected 3 to 10 minutes after initiation of the transverse electrophoresis, respectively) was then subjected to analytical electrophoresis in order to determine the quantity and size of the DNA recovered.

The analytical electrophoresis showed that samples taken at times 3, 4, and 5 minutes after the start of the transverse electrophoresis contained no detectable DNA. The sample collected after 6 minutes contained some of the 48.5, 23.1, 9.4, 6.6, and 4.4 kb DNA fragments. The sample collected after 7 minutes contained slightly more of the same five DNA fragments as the sample collected after 6 minutes, while the samples collected after 8, 9, and 10 minutes contained progressively decreasing amounts of these 5 DNA fragments. Based on a visual examination of the analytical gel (i.e., by comparing the relative intensity of the sample taken after 7 minutes with a λDNA internal standard), it was estimated that the sample taken after 7 minutes represented about 10% of the DNA initially loaded onto the preparative gel.

Based on the above experimental findings, several observations can be made. The fact that there was more DNA in the sample taken after 7 minutes than in the samples taken either before or after that time reflects that before 7 minutes the DNA molecules had not yet reached the recovery well, and that after 7 minutes the DNA that was in the recovery well was beginning to leave the well. The fact that DNA fragments smaller that 4.4 kb (i.e., the 2.2 and 2.0 kb fragments) were not detected indicates that they were lost because they had migrated past the point at which the transverse electrophoresis would move the material into the recovery well, i.e., the trajectory of the smaller fragments during transverse electrophoresis did not intercept the recovery well.

Example 3

Purification of Genomic DNA From Blood by Single-Direction Multi-Well Preparative Electrophoresis Nucleic Acid Sample.

To prepare the blood sample for purification, the blood sample was mixed with a lysis buffer then the blood/lysis buffer mixture was incubated at an elevated temperature. The blood/lysis buffer mixture was formed by mixing 10 µL of fresh blood, i.e., less than one month old, with 30 µL of lysis buffer and 3.6 µL of Proteinase K (20 mg/mL), where 1.4 mL of lysis buffer consisted of 1 mL of 110 mM Tris-HCl (pH 8.3), 250 mM NaCl, 19 mM sarkosyl detergent, 0.05% Nonidet P-40, and 0.4 mL of 2-pyrrolidinone. The blood/lysis buffer mixture was then incubated at 65° C. for 35 minutes in 0.5 mL tubes.

Electrophoresis Apparatus and Conditions.

The electrophoresis matrix was an 0.8% agarose gel, and was made as described above. The gel was 2.2×11.7 cm. The loading wells were 1 mm thick and 5 mm wide. The recovery wells were 2 mm thick and 5 mm wide. The recovery wells were located 5 mm from the loading wells. Both the gel and tank buffer were 0.2× TAE.

Electrophoresis was performed in a 27.2×12 cm H5 gel electrophoresis tank (Gibco BRL, Life Technologies) and the forward electric field had a magnitude of 10.6V/cm. The electric field across the gel, and the temperature of the gel tank buffer, were measured using a Model 2706 multimeter (BK Precision, Chicago, Ill.). 870 mL of buffer was added to the tank, an amount sufficient to submerge the gel under a 5 mm layer of buffer.

Electrophoresis Protocol.

Three nucleic acid samples (20µL of lysed and digested blood each) were loaded into a first set of three adjacent loading wells. Forward electrophoresis (at 10.6V/cm) was performed for 1 minute, after which time the electric field was interrupted and a second set of 3 DNA samples were loaded into a second set of three adjacent loading wells. Another three sets of three DNA samples each were loaded into three more sets of loading wells in the same fashion for a total of 15 DNA samples loaded at 1 minute intervals. Electrophoresis (at 10.6V/cm) was performed for 16 minutes after loading the last set of samples. These five sets of three samples each therefore corresponded to samples that had migrated 20, 19, 18, 17, and 16 minutes, respectively.

Following the initial forward electrophoresis, the gel was stained with EtBr and examined visually. This examination revealed that most of the DNA present in the samples that had migrated for 16, 17, and 18 minutes had not reached their corresponding recovery wells, that the DNA present in the samples that had migrated for 19 minutes had reached their corresponding recovery wells, and that the DNA present in the samples that had migrated for 20 minutes had migrated through their corresponding recovery wells.

Based on the above experimental findings, several observations can be made. First, there is an optimal migration time that must be carefully controlled in order for this method to be successful, i.e., the DNA will not reach the recovery well if the electrophoresis time is too short, and the DNA will migrate past the recovery well if the electrophoresis time is too long. Second, yield of recovered purified nucleic acid is low (about 15%) because, even at the optimal time, e.g., 19 minutes in this example, much of the DNA is still located in the gel between the loading and recovery wells. Another factor responsible for the low recovery is that a large proportion (maybe up to 50%) of the DNA loaded in the loading well never leaves the loading well. This is likely due to the fact that this immobile DNA is too large to enter the gel. Yet another factor responsible for the low recovery is that the level of the buffer in the gel electrophoresis tank was not lowered such that buffer no longer covered the gel.

Example 4

Purification of Genomic DNA From Blood by Single-Direction Multi-Well Preparative Electrophoresis using a LITAC Electrical Field Nucleic Acid Sample.

The nucleic acid was prepared as described in Example 3 above.

Electrophoresis Apparatus and Conditions.

The electrophoresis matrix, well geometry and location, and gel box apparatus were as described in Example 3 above. The LITAC electric field profile is described immediately below.

Electrophoresis Protocol.

Sixteen nucleic acid samples (20 µL of lysed and digested blood each containing approximately 80 ng of human genomic DNA) were loaded into adjacent wells. DC forward electrophoresis at 13.2V/cm was performed for a period of 17 minutes, after which time the forward electric field was changed from a DC field to a LITAC field. The LITAC profile comprised a forward portion having a duration of 40 seconds and a field strength of −6.9V/cm, and a reverse portion having a duration of 20 seconds and a field strength of 13.8V/cm. This LITAC regime was applied for a total time of 150 minutes. 100 µL purified nucleic acid samples were collected from each of the recovery wells at ten minute intervals after initiating the LITAC electrophoresis.

The sixteen 100 µL purified nucleic acid samples were lyophilised and resuspended in 21 µL of water. The samples corresponding to LITAC times of 0, 20, 40, 60, 80, 100, 120, and 140 minutes were subjected to analytical electrophoresis in order to determine the quantity and size of the recovered purified nucleic acid. This analytical electrophoresis indicated that samples taken at LITAC times of 0 and 20 minutes did not contain enough human genomic DNA to be visible on a EtBr stained gel, that the sample taken at a LITAC time 40 minutes contained a barely visible amount (roughly 1 ng) of human genomic DNA, and that samples taken at LITAC times of 60, 80, 100, 120, and 140 minutes each contained roughly 20 ng of human genomic DNA. All purified DNA molecules were larger than 48.5 kb.

The LITAC pulses employed here provide a significant improvement to the method described in Experiment 3 above because DNA that reaches the recovery well is trapped in the recovery well rather than migrating through the well. This is evidenced by the fact that samples taken at LITAC times of 60, 80, 100, 120, and 140 minutes all contained the approximately the same amount of DNA. The yield of purified nucleic acid is still relatively low, i.e., about 25% in this Example, because a large proportion (maybe up to 50%) of the DNA loaded in the loading well never leaves this well. This is likely due to the fact that this DNA is too large to enter the gel.

Example 5

Purification of Genomic DNA From Blood by Trapping Preparative Electrophoresis using a LITAC Reverse Electrical Field Nucleic Acid Sample.

The nucleic acid sample was prepared essentially as described above in Example 3 above, except that 10 $\mu$l of fresh blood was mixed with 60 $\mu$L of lysis buffer rather than 30 $\mu$l of lysis buffer, and the lysis buffer contained 125 mM NaCl rather than 250 mM NaCl.

Electrophoresis Apparatus and Conditions.

The electrophoresis matrix was a 2.0% agarose gel, and was made with Molecular Biology grade agarose from Promega. The gel was 2.2×11.7 cm and included a single set of loading/recovery wells located in the middle of the gel. The wells were 1 mm thick and 5 mm wide. The gel protruding around the wells due to the capillary action between the well-forming comb and the liquid agarose was removed using a razor blade to produce a gel having a uniformly flat surface. Both the gel and tank buffer were 0.2× TAE.

Electrophoresis was performed in a 27.2 cm long and 12 cm wide H5 gel electrophoresis tank (Gibco BRL, Life Technologies). The electric field across the gel, and the temperature of the gel tank buffer, were measured using a Model 2706 multimeter (BK Precision, Chicago, Ill.). 870 mL of buffer was added to the electrophoresis tank. This amount of buffer was sufficient to submerge the gel under a 5 mm thick layer of buffer.

Electrophoresis Protocol.

Nine nucleic acid samples (22 $\mu$L of lysed and digested blood each containing approximately 80 ng of human genomic DNA) were loaded into adjacent wells. DC forward electrophoresis (at 10.5V/cm) was performed for 18 minutes. A reverse DC field of 10.5 V/cm was then applied for 30 seconds. Two 22 $\mu$L samples were then collected from two of the three wells (samples #1 and #2). Next, in order to improve the recovery of DNA from the gel, LITAC pulses of 15 seconds at −10.5V/cm and 30 seconds at 5.0V/cm were applied for 12 minutes. Seven 22 $\mu$L samples were then collected from the other seven wells (samples #3 to #9).

Samples #1, 2, 3, and 9 were subjected to analytical electrophoresis in order to determine the quantity and size of the purified nucleic acid. This analytical gel showed that the two samples taken at LITAC times of 0 minutes (samples #1 and #2) contained only about half of the DNA contained in samples collected after 12 minutes of LITAC pulses (samples #3 and #9). Visual examination of the EtBr DNA bands corresponding to samples #3 and #9 (relative to known amounts of λ-phage DNA) indicated that roughly 50 ng of DNA had been recovered in these two samples. This represents a yield of about 55% of the human genomic DNA initially loaded. All purified DNA molecules were larger than 48.5 kb.

To determine the quality of the purified nucleic acid, PCR amplifications were performed using the purified nucleic acid as the template. Standard PCR conditions were used to perform the PCRs. Strong PCR amplification products (a DNA fragment of about 400 bp) were observed whether we used undiluted purified nucleic acid or whether we diluted the purified nucleic acid 1, 2, 3, 4, or 5 fold. This shows that the DNA purified using our method is both relatively free of any contaminants (because dilution was not required for the PCR amplification to work), and, that the purified nucleic acid was relatively concentrated (because a strong signal was obtained even when the purified nucleic acid was diluted).

The relatively high recovery achieved here (close to 50%) can be explained by the fact that this method is a one well method which allows recovery of large DNA molecules that never enter the gel.

Example 6

Purification of Genomic DNA From Blood by Trapping Preparative Electrophoresis using a Horizontal Dry-Gel Format Nucleic Acid Sample.

The nucleic acid sample was prepared essentially as described in Example 3 above, except that the lysis buffer contained 125 mM rather than 250 mM NaCl.

Electrophoresis Apparatus and Conditions.

The electrophoresis matrix was a 2.0% agarose gel, and was made with SeaKem Gold agarose sold by FMC Corporation. The gel was 2.0×2.0 cm, and 0.6 cm thick. The gel included a single set of three wells located in the middle of the gel. The three wells of this gel were 1 mm long, 3.8 mm wide, and 5 mm deep. As previously described, gel protruding around the wells was removed using a razor blade to produce a gel with a surface that was uniformly flat.

Instead of filling the electrophoresis tank with buffer, two rectangular buffer-saturated sponges were used to effect electrical contact between the electrodes and the gel. These sponges were located on both side of the gel and placed in direct contact with both the gel and the electrodes. The sponges were 5 cm long, 2 cm wide (i.e., the same width as the gel width), and 1 cm thick (i.e., 4 mm higher than the gel). They were made by cutting cosmetic sponges sold by CAROLINE Cosmetics (Montreal, Canada). Both the gel and sponge buffer were 0.2× TAE (unadjusted pH of 7.8).

Electrophoresis was performed in the middle part of a 27.2×12 cm H5 gel electrophoresis tank (Gibco BRL, Life Technologies). To properly position the electrodes with respect to the sponges and the gel, the electrodes were unscrewed from the walls of the electrophoresis tank and placed in contact with the sponges using clamps. The electric field across the gel was measured using a Model 2706 multimeter (BK Precision, Chicago, Ill.).

Electrophoresis Protocol.

Three DNA samples (20 $\mu$L of lysed and digested blood each containing approximately 80 ng of human genomic DNA) were loaded in adjacent wells. DC electrophoresis was performed in the forward direction for 25 minutes, followed by DC electrophoresis in the backwards direction for 40 seconds. A voltage of 95 volts was applied in both the forward and backward electrophoresis. During the electrophoresis, the actual voltage across the gel, excluding the voltage drops across the sponges, varied between 7 and 8 V/cm. 20 µL purified nucleic acid samples were then collected from each of the three wells (samples #1, #2, and #3).

Sample #1 was subjected to analytical electrophoresis in order to determine the quantity and size of the recovered purified nucleic acid. Visual examination of the EtBr DNA band corresponding to sample #1 (relative to known amounts of λ-phage DNA) indicated that roughly 30 ng of DNA had been recovered in this sample. This represents an overall yield of about 38% of the human genomic DNA initially loaded. These purified DNA molecules were larger than 48.5 kb.

PCR tests were performed to determine the quality of the DNA purified using the electrophoretic purification method described above. Standard PCR protocols were used to perform the PCRs. Strong amplification products (a DNA fragment of about 400 bp) were observed whether we used undiluted purified DNA from sample #2, or whether we diluted the sample 1 fold.

Example 7

Purification of Genomic DNA From Blood by Trapping Preparative Electrophoresis using a Vertical Dry-Gel Format Nucleic Acid Sample.

The nucleic acid sample was prepared as described above in Example 3 above except that the NaCl concentration was lowered from 250 mM to 125 mM in order to decrease the amount of ions present in the lysed blood samples. It has been established that such a reduction in the amount of NaCl does not significantly decrease the amount of DNA recovered, but tends to lead to more consistent purification results.

Electrophoresis Apparatus and Conditions.

The electrophoresis matrix used was a 2% agarose gel, and was made with SeaKem Gold agarose sold by FMC Corporation. The cylindrical gel was 3.8 cm in diameter and 8 cm high. The gel was formed in a 8 cm high transparent Plexiglas tube with an internal diameter of 3.8 cm and an external diameter of 4.5 cm. The Plexiglas tube acted as a gel tray and was not removed during electrophoresis. The "comb" used to make the loading/recovery wells consisted of twelve 2.5 cm long polypropylene rods glued to a flat piece of Plexiglas, each rod having a diameter of 5 mm. These twelve rods were disposed, with a 9 mm distance between the center of each rod, in the following pattern:

|   | X | X |   |
|---|---|---|---|
| X | X | X | X |
| X | X | X | X |
|   | X | X |   |

The wells made with this comb were 5 mm in diameter and 1.5 cm deep, and were separated from one another by 4 mm of gel. The gel buffer was 0.2× TAE.

The electrode configuration consisted of two platinum wire grids at each end of the cylindrical gel. These grids were made by drilling 5 mm diameter holes in plastic sheets (at the same location as that of the wells in the gel) and weaving platinum wire between these holes. The electric field across the gel was measured using a Model 2706 multimeter (BK Precision, Chicago, Ill.).

Electrophoresis Protocol.

100 µL DNA samples were loaded in each of the four central wells. The electrophoresis was carried out using three consecutive regimes: 1) a first pulsed field regime having a pulse program consisting of 30 seconds at 46 V forward electric field followed by 10 seconds at 46 V reverse electric field, applied for a total of 10 minutes; 2) a second pulsed field regime having a pulse program consisting of 30 seconds at 28 V forward electric field followed by 10 seconds at 46 V reverse electric field, applied for a total of 160 minutes; and 3) a reverse DC regime comprising a reverse field of 46 V applied for 2 minutes. At the conclusion of the electrophoresis, the electric field was turned off and a 70 µL sample was recovered from one of the four central wells.

10 µL of the recovered purified nucleic acid was subjected to analytical electrophoresis in order to determine its quantity and size. The controls loaded on the analytical gel were samples containing 5, 12.5, 25 and 50 ng of uncut λ-phage DNA (48.5 kb long). Visual inspection of the analytical gel showed that the purified nucleic acid was larger that 48.5 kb and that our sample contained about 0.5 ng/µL of human genomic DNA.

The relative purity of the DNA contained in this sample was estimated by visually comparing the intensity of PCR bands obtained by serial dilutions of pure human DNA, human DNA present in lysed and Proteinase K digested (but unpurified) blood samples, and our purified human DNA sample. These PCR reactions were performed using the D7S-550 primers (Perkin Elmer), the Stockmarks buffer (Perkin Elmer), and AmpliTaq DNA polymerase (Perkin Elmer). This experiment showed that the concentration of contaminants present in unpurified (but lysed and Proteinase K digested human blood) samples was reduced by a factor of at least 50 times in the purified nucleic acid.

Example 8

Perparation and Use of Agarose/Polypropylene Composite Electrophoresis Matrix

Nucleic Acid Sample.

The nucleic acid sample was prepared essentially as described above in Example 3 above, except that 60 µl of lysis buffer was used.

Preparation of Composite Matrix.

A polypropylene sheet, which was 0.0625 inches thick with 120 micron pore size, was cut into a 11 cm wide and 2 cm long strip. A row of 6 wells were made in the middle of the strip. Each well was 5 mm wide, 1.5 mm long and 5 mm deep. There was therefore about 1.5 mm of plastic material at the bottom of the wells. The distance from the centre of one well to the next was 16 mm.

The plastic strip was soaked in 70% ethanol for 5 minutes before it was used. 100 mL of 3% SeaKem Gold agarose containing 0.2× TAE pH 7.9 was boiled for one minute and cooled down for 5 minutes at room temperature. It was then mixed well and boiled again for 5 minutes. This procedure was then repeated a third time and distilled water was added to replace the water that had evaporated. This insured that the agarose solution was homogenous and well dissolved. The plastic strip soaked with 70% ethanol was dropped into the hot agarose liquid, shaken well, and then boiled in a microwave for 3 minutes.

The hot liquid agarose and plastic strip were transferred into a sealed gel tray (14 cm long, 11.2 cm wide and 2 cm deep) and the agarose was left at room temperature to solidify for about 1 hour. The plastic strip was placed in the middle of the gel tray in order to have 2.5 cm of agarose on either side of it. Once the agarose had solidified, the gel containing the plastic strip was removed from the tray and this gel was cut into a gel piece of 11.2 cm in width and 7 cm in length (i.e., 2.5 cm of agarose gel, 2 cm of plastic strip, and another 2 cm of agarose gel). The agarose present in the wells was removed using a needle. Also note that the upper and lower surfaces of the plastic strip was covered by a 1 mm layer of agarose.

Electrophoresis Apparatus and Conditions.

Electrophoresis was performed in a 27.2 cm long and 12 cm wide H5 gel electrophoresis tank (Gibco BRL, Life Technologies). 870 mL of 0.2× TAE pH7.9 buffer was added into this tank. This amount of buffer was enough to have a 5 mm thick region of buffer covering the gel containing the plastic strip.

The electric field across the whole gel and the plastic strip were measured using a Model 2706 multimeter (BK Precision, Chicago, Ill.). When an electric field of 117 Volts was applied, it was found that the electric field across the whole gel was 6.6V/cm, and that the electric field across the plastic strip was 9V/cm. This indicates that resistance is higher in the plastic strip (containing agarose) than in the sections of pure agarose on either side of it.

Electrophoresis Protocol.

25 uL of 250 mM NaCl-containing lysed blood was loaded into each of 6 wells. A DC forward field of 9V/cm across the plastic strip was applied for 60 minutes. 28 uL of purified DNA sample was collected from each of the first 3 wells (samples 1, 2, and 3). A DC backward field of −9V/cm was then applied for one minute, and another three 28 uL samples were collected from the remaining 3 wells (samples 4, 5, and 6). The whole gel was stained in EtBr solution. It was found that the fluorescence background of plastic strip was higher than that of the agarose gel, and that the fluorescence background inside of the wells (which were inside the plastic strip) was higher than in the body of the plastic strip.

20 uL of samples 1 and 4 were loaded on a 0.4% SeaKem Gold agarose gel. Visual examination of the EtBr DNA bands corresponding to these two samples (relative to known amounts of lambda DNA) indicated that roughly 25 ng of DNA bands had been recovered in each 20 uL of collected samples. This represents a yield of about 35% the human genomic DNA initially loaded. (35%=((25 ng/20 uL )×28 uL)/(25 uL×4 ng/uL)).

All publications and patent applications are herein incorporated by reference to the same extent as if each individual publication or patent application was specifically and individually indicated to be incorporated by reference.

Although only a few embodiments have been described in detail above, those having ordinary skill in the biochemical art will clearly understand that many modifications are possible in the preferred embodiment without departing from the teachings thereof. All such modifications are intended to be encompassed within the appended claims.

We claim:

1. A method for purifying a nucleic acid sample comprising the steps of:

providing a nucleic acid sample comprising a desired nucleic acid and one or more contaminants;

providing an electrophoresis matrix having a loading/recovery well formed therein;

placing the nucleic acid sample into the loading/recovery well;

performing a first electrophoresis comprising electrophoresing the nucleic acid sample for a first time effective to transport the desired nucleic acid out of the loading/recovery well and into the electrophoresis matrix; and performing a second electrophoresis comprising electrophoresing the nucleic acid sample for a second time effective to transport the desired nucleic acid out of the electrophoresis matrix and back into the loading/recovery well;

wherein the first and second electrophoresis is effective to substantially reduce the concentration of contaminants relative the concentration of desired nucleic acid, thereby producing a purified nucleic acid.

2. The method of claim 1 wherein the matrix comprises a bulk portion and a well-matrix-interface portion, the matrix being effective to trap the desired nucleic acid in the well-matrix-interface portion during the first electrophoresis such that the desired nucleic acid is substantially prevented from entering the bulk portion of the matrix.

3. The method of claim 2 wherein the first time is greater than the second time.

4. The method of claim 3 wherein the first time is equal to or greater than 20 minutes and the second time is less than or equal to 30 seconds.

5. The method of claim 2 wherein the second electrophoresis employs a LITAC electrical field comprising a forward time $t_F$, a forward electrical field $E_F$, a reverse time $t_R$, and a reverse electrical field $E_R$, wherein (a)

$$t_F{}^*E_F = t_R{}^*E_R,$$

and (b) the forward electrical field $E_F$ is greater than the reverse electrical field $E_R$.

6. The method of claim 1 wherein the first electrophoresis is sufficient to transport a portion of the contaminants out of the loading well, through the electrophoresis matrix, and into a contaminant dilution reservoir, the reservoir containing a volume of buffer sufficient to substantially dilute the contaminants entering the reservoir.

7. The method of claim 1 wherein the first electrophoresis employs a DC electrical field and the second electrophoresis employs a LITAC electrical field comprising a forward time $t_F$, a forward electrical field $E_F$, a reverse time $t_R$, and a reverse electrical field $E_R$, wherein (a)

$$t_F{}^*E_F = t_R{}^*E_R,$$

and (b) the forward electrical field $E_F$ is treater than the reverse electrical field $E_R$.

8. The method of claim 7 wherein the LITAC electrical field comprises a forward electrical field having a magnitude $E_f$, and a reverse electrical field having a magnitude $E_r$, wherein the ratio $E_f/E_r$ is greater than 2.

9. The method of claim 8 wherein the LITAC electrical field comprises a forward electrical field having a magnitude $E_f$, and a reverse electrical field having a magnitude $E_r$, wherein the ratio $E_f/E_r$ is approximately 2.4.

10. A method for purifying a nucleic acid sample comprising the steps of:

providing a nucleic acid sample comprising a desired nucleic acid and one or more contaminants;

providing an electrophoresis matrix having a loading well and a recovery well formed therein, wherein the loading well and the recovery well are separate wells;

placing the nucleic acid sample into the loading well;

performing a first electrophoresis comprising electrophoresing the nucleic acid sample for a first time effective to transport the desired nucleic acid out of the loading well and into the electrophoresis matrix; and performing a second electrophoresis comprising electrophoresing the nucleic acid sample for a second time effective to transport the desired nucleic acid out of the electrophoresis matrix and into the recovery well;

wherein the first electrophoresis employs a DC electrical field and the second electrophoresis employs a LITAC electrical field comprising a forward time $t_F$ a forward electrical field $E_F$, a reverse time $t_R$, and a reverse electrical field $E_R$, wherein (a)

$$t_F * E_F = t_R * E_R,$$

and (b) the forward electrical field $E_F$ is greater than the reverse electrical field $E_R$;

wherein the first and second electrophoresis is effective to substantially reduce the concentration of contaminants relative the concentration of desired nucleic acid, thereby producing a purified nucleic acid.

11. The method of claim 10 wherein the LITAC electrical field comprises a forward electrical field having a magnitude $E_f$, and a reverse electrical field having a magnitude $E_r$, wherein the ratio $E_f/E_r$ is greater than 2.

12. The method of claim 11 wherein the LITAC electrical field comprises a forward electrical field having a magnitude $E_f$, and a reverse electrical field having a magnitude $E_r$, wherein the ratio $E_f/E_r$ is approximately 2.4.

13. A method for purifying a nucleic acid sample comprising the steps of:

providing a nucleic acid sample comprising a desired nucleic acid and one or more contaminants;

providing an electrophoresis matrix having a loading well and a recovery well formed therein, wherein the loading well and the recovery well are separate wells;

placing the nucleic acid sample into the loading well;

performing a first electrophoresis comprising electrophoresing, the nucleic acid sample for a first time effective to transport the desired nucleic acid out of the loading well and into the electrophoresis matrix; and performing a second electrophoresis comprising electrophoresing, the nucleic acid sample for a second time effective to transport the desired nucleic acid out of the electrophoresis matrix and into the recovery well;

wherein the first electrophoresis comprises electrophoresing the desired nucleic acid in a first direction and the second electrophoresis comprises electrophoresing the desired nucleic acid in a second direction different from the first direction and wherein the first and second electrophoresis is effective to substantially reduce the concentration of contaminants relative the concentration of desired nucleic acid, thereby producing a purified nucleic acid.

14. The method of claim 13 wherein the first electrophoresis employs a DC electrical field and the second electrophoresis employs a LITAC electrical field comprising a forward time $t_F$, a forward electrical field $E_F$, a reverse time $t_R$, and a reverse electrical field $E_R$, wherein (a)

$$t_F * E_F = t_R * E_R,$$

and (b) the forward electrical field $E_F$ is greater than the reverse electrical field $E_R$.

15. The method of claim 14 wherein the LITAC electrical field comprises a forward electrical field having a magnitude $E_f$, and a reverse electrical field having a magnitude $E_r$, wherein the ratio $E_f/E_r$ is greater than 2.

16. The method of claim 15 wherein the LITAC electrical field comprises a forward electrical field having a magnitude $E_f$, and a reverse electrical field having a magnitude $E_r$, wherein the ratio $E_f/E_r$ is approximately 2.4.

* * * * *